United States Patent [19]
Makishima et al.

[11] Patent Number: 5,827,878
[45] Date of Patent: Oct. 27, 1998

[54] PHARMACEUTICAL COMPOSITION FOR THE TREATMENT OF LEUKEMIA CONTAINING 9-CIS-RETINOIC ACID-α-TOCOPHEROL ESTER

[75] Inventors: Makoto Makishima, Saitama-ken; Yasuhiro Kanatani, Tokorozawa; Yoshio Honma, Saitama-ken; Kohei Inomata; Takao Kishiye, both of Saitama-ken, all of Japan

[73] Assignee: Nisshin Flour Milling Co., Ltd., Tokyo, Japan

[21] Appl. No.: 884,040

[22] Filed: Jun. 27, 1997

[30] Foreign Application Priority Data

Jul. 1, 1996 [JP] Japan ................................ 8-171028

[51] Int. Cl.$^6$ .................................................. A61K 31/355
[52] U.S. Cl. ............................................................ 514/458
[58] Field of Search ............................................... 514/458

[56] References Cited

U.S. PATENT DOCUMENTS 3,878,202   4/1975   Fukawa et al. ..................... 260/240 H

FOREIGN PATENT DOCUMENTS

| 0 008 573 | 3/1980 | European Pat. Off. . |
|---|---|---|
| 4-244076 | 9/1992 | Japan . |
| 5-202020 | 8/1993 | Japan . |
| 7-2674 | 1/1995 | Japan . |

OTHER PUBLICATIONS

Makoto Makishima, et al., Blood, vol. 87, No. 8, pp. 3384–3394, "Enhancement of Activity of 1α, 25–Dihydroxyvitamin $D_3$ for Growth Inhibition and Differentiation Induction of Human Myelomonocytic Leukemia Cells by Tretinoin Tocoferil an α–Tocopherol Ester of All–Tans Retinoic Acid".

A. Verstuyf, et al., Proc. Workshop Vitamin D, vol. 9, No. Vitamin D, pp. 449–450, 1994, "Terminal Differentiation of Human Leukimia Cells (HL60) by a Combinbation of 1,25–Dihydroxyvitamin $D_3$ and Retnoic Acid (All Trans or 9–Cis)".

Database WPI, Derwent Publication, AN 92–337748, JP 04–244076, Sep. 1, 1992.

M. Lanotte, et al., "NB4, A Maturation Inducible Cell Line with t(15;17) Marker Isolated from a Human Acute Promyelocytic Leukemia (M3)", Blood, vol. 77, No. 5, Mar. 1, 1991: pp. 1080–1086.

Raymond P.Warrell, Jr.,et al., "Acute Promyelocytic Leukemia", The New England Journal of Medicine, vol. 329, No. 3, Jul. 15, 1993, pp. 177–189.

Martin Petkovich, et al., "A Human Retinoic Acid Receptor Which Belongs to the Family of Nuclear Receptors", Nature, vol. 330, Dec. 3, 1987, pp. 444–450.

Akiko Sakashita, et al., "9–Cis–Retinoic Acid: Effects on Normal and Leukemic Hematopoiesis in Vitro", Blood, vol. 81, No. 4, Feb. 15, 1993: pp. 1009–1016.

Vincent Giguere, et al., Identification of a Receptor for the Morphogen Retinoic Acid, Nature, vol. 330, Dec. 17, 1987: pp. 624–629.

H. Phillip Koeffler, et al., 1,25–Dihydroxyvitamin D3: In Vivo and In Vitro Effects on Human Preleukemic and Leukemic Cells, Cancer Treatment Reports, vol. 69, No. 12, Dec. 1985, 1399–1407.

Daniel D. Bikle, "Clinical Counterpoint: Vitamin D: New Actions, New Analogs, New Therapeutic Potential", Endocrine Reviews, vol. 13, No. 4, pp. 765–784.

Raymond P. Warrell, Jr. "Retinoid Resistance in Acute Promyelocytic Leukemia: New Mechanisms, Strategies, and Implications", Blood, vol. 82, No. 7, Oct. 1, 1993: pp. 1949–1953.

Richard A. Heyman, et al., "9–Cis Retinoic Acid is a High Affinity Ligand for the Retinoid X Receptor", Cell, vol. 68, Jan. 24, 1992, pp. 397–406.

M. Makishima, et al., International Journal of Hematology, Supplement No. 1, Apr. 1997, vol. 65, p. 41, "Differentiation Therapy with Novel Retinoid Analogs" Translated part only.

*Primary Examiner*—Jerome D. Goldberg
*Attorney, Agent, or Firm*—Oblon, Spivak, McClelland, Maier & Neustadt, P.C.

[57] ABSTRACT

9-Cis-retinoic acid-α-tocopherol esters, pharmaceutical compositions containing the same and use of the same as a medicine for the treatment of leukemia, in particular, the remission of leukemia are provided and a combined use of a 9-cis-retinoic acid-α-tocopherol ester and either 1α,25-dihydroxyvitamin $D_3$ or 9-cis-retinoic acid exhibits a synergistic effect in the treatment of leukemia without any side effects caused by 1α,25-dihydroxyvitamin $D_3$ or 9-cis-retinoic acid.

3 Claims, 5 Drawing Sheets

PHARMACEUTICAL COMPOSITION FOR THE TREATMENT OF LEUKEMIA CONTAINING 9-CIS-RETINOIC ACID-α-TOCOPHEROL ESTER

FIELD OF THE INVENTION

This invention relates to a pharmaceutical composition for the treatment of leukemia containing 9-cis-retinoic acid-α-tocopherol ester and a method for the treatment of leukemia administering the same. It is further concerned with a pharmaceutical composition for the treatment of leukemia containing as an active ingredient the said compound alone or in combination with either 1α,25-dihydroxyvitamin $D_3$ (hereinafter referred to as "$VD_3$") or 9-cis-retinoic acid (hereinafter referred to as "9-cis-RA"). Further it is concerned with a method for the treatment of leukemia administering 9-cis-retinoic acid-α-tocopherol ester together with $VD_3$ or 9-cis-RA.

BACKGROUND OF THE INVENTION

Cancers, among various diseases, have recently taken the first position of causes of death and there has been desired an earlier development and establishment of a novel therapy against cancers. In particular, there has been attempted a therapy against leukemia, a blood cancer, using agents having an inhibitory action on the proliferation of leukemia cells and an inducing action on the differentiation of the said cells. It is known that the differentiation induction of leukemia cells into mature leukocyte-like cells may inhibit the proliferation of leukemia cells, which leads to loss of properties of leukemia cells.

It is reported that the treatment with natural type of a retinoid, all-trans retinoic acid (hereinafter referred to as "ATRA"), brings complete remission in 90% or more of the patients suffering from acute promyelocytic leukemia with PML/RARα transposition (New Eng. J. Med., Vol. 329, 177, 1993).

Recently, a retinoic acid receptor (hereinafter referred to as "RAR") has been found to be a receptor for ATRA (Nature, Vol. 330, 440, 1987 and ibid., Vol. 330, 624, 1987), and it is believed that ATRA would perform various transcriptional controls via RAR. However, relapses have frequently occurred in therapy using ATRA and, in the case of relapses after the treatment with ATRA, a re-remission rate by ATRA has been lowered to 36%. Moreover, ATRA may exhibit severe side effects and, when administered at a high dose, various disturbances have been induced in the skin, central nervous system, liver and so on. Furthermore, administration of ATRA to pregnant women would accompany a risk of teratogenesis. Accordingly, patients may have to face the problem to obviate those disturbances caused by a high dose. It is also known that continuous administration of ATRA induces binding proteins such as intracellular ATRA-binding protein (CRABP) and consequently a serum ATRA concentration may be reduced to eventuate in unfavorable results in view of the purpose of leukemia therapy (Blood, Vol. 82, 1949, 1993).

Recently, a new retinoid receptor, retinoid X receptor (hereinafter referred to as "RXR"), has been found and its ligand has been identified as 9-cis-RA which is a geometrical isomer of ATRA at the 9-position thereof (Cell, Vol. 68, 397, 1992). 9-cis-RA is known to be a strong ligand for not only RXR but also RAR, having a differentiation inducing activity in HL-60 cells of myelocytic leukemia cells ("IGAKU NO AYUMI", Vol. 175, 925, 1995 and Blood, Vol. 81, 1009, 1993).

However, 9-cis-RA is also known to be chemically unstable and easily isomerized to ATRA, from which similar side effects to those of ATRA may be expected. Thus, a possibly reduced dose of 9-cis RA has been desired.

On the other hand, $VD_3$ known as an agent for improving bone metabolism has a cell differentiation inducing activity as ATRA does and induces the differentiation of those cells derived from colon cancer, breast cancer and leukemia (Endocrine Rev., Vol. 13, 765, 1992). Use of $VD_3$ as an anticancer agent is also expected. However, $VD_3$ is applicable only at a lower dose. For example, a serum $VD_3$ concentration beyond $10^{-9}$M may give rise to side effects such as hypercalcemia and others. Therefore, a clinical use of such a dose to cause a high $VD_3$ concentration in the serum has been restricted (Cancer Treat. Rep., Vol. 69, 1399, 1985).

For combination of ATRA with $VD_3$, Japanese Patent Kokai 7-2674 describes under the item of the prior art that a combined use of both compounds could produce only additive effect on the inhibition of growth and differentiation induction of HL-60 leukemia cells. The publication discloses a therapeutic agent for leukemia which comprises ATRA and a $VD_3$ analogue in order to achieve a synergistic effect. However, it is apparent from Table 1 of the publication that a serum concentration of the $VD_3$ analogue should be $10^{-8}$M or more in order to accomplish 50% or more growth inhibition rate of leukemia cells. The use of $VD_3$ at such a high concentration would produce possible side effects such as severe hypercalcemia as described above.

Our Japanese Patent Kokai 4-244076 discloses an esterified product of 9-cis-RA and a tocopherol derivative is useful for the treatment of skin ulcers, peptic ulcers and tumours. However, it does not disclose the ester is useful as a therapeutic agent for leukemia.

Under these circumstances, there has been desired a development of a novel and effective therapeutic agent for leukemia with less side effects on a living body, but a satisfactorily effective medicine has not yet been found out up to the present time. In view of this, there has been a need for a novel compound for use as a therapeutic agent for leukemia having a more potent therapeutic effect and a higher safety as compared with the prior art therapeutic agents for leukemia.

BRIEF SUMMARY OF THE INVENTION

We have made earnest studies in order to solve the problems as discussed above and finally have found that 9-cis-retinoic acid-α-tocopherol ester, which is an α-tocopherol ester of 9-cis-RA as a composition of matter, can exhibit a differentiation inducing activity of leukemia cells, and further that a combined use of 9-cis-retinoic acid-α-tocopherol ester with $VD_3$ or 9-cis-RA is very effective for treating leukemia at such a low dose of $VD_3$ or 9-cis-RA that does not produce side effects on a living body. This invention has been completed upon these findings.

DETAILED DESCRIPTION OF THE INVENTION

This invention relates to a pharmaceutical composition for the treatment of leukemia which comprises as an active ingredient a 9-cis-retinoic acid-α-tocopherol ester represented by the formula (I)

and a pharmaceutical carrier thereof.

Moreover, this invention relates to a pharmaceutical composition for the treatment of leukemia which comprises as an active ingredient a combination of a 9-cis-retinoic acid-α-tocopherol ester represented by the above formula (I) with $VD_3$.

Furthermore, this invention relates to a pharmaceutical composition for the treatment of leukemia which comprises as an active ingredient a combination of a 9-cis-retinoic acid-α-tocopherol ester represented by the above formula (I) with 9-cis-RA.

This invention also relates to a method for the treatment of leukemia which comprises administering to a patient suffering from leukemia a therapeutically effective amount of a 9-cis-retinoic acid-α-tocopherol ester represented by the above formula (I).

Further, the invention relates to a method for the treatment of leukemia which comprises administering to a patient suffering from leukemia a therapeutically effective amount of 9-cis-retinoic acid-α-tocopherol ester together with $VD_3$ at a sufficiently low dose not to produce side effects.

Furthermore, the invention relates to a method for the treatment of leukemia which comprises administering to a patient suffering from leukemia a therapeutically effective amount of 9-cis-retinoic acid-α-tocopherol ester together with 9-cis-RA at a sufficiently low dose not to produce side effects.

Japanese patent publication 60-56156 discloses that 9-cis-retinoic acid-α-tocopherol ester can be obtained by light-isomerisation of all-trans α-tocopherol vitamin A acid. Commercially it may be prepared by an esterification of 9-cis-RA with α-tocopherol. The esterification of 9-cis-RA with α-tocopherol may be carried out according to any well-known esterification processes, for example, the process as disclosed in our Japanese Patent Kokai 5-202020.

The term "α-tocopherol" as used herein refers to dl-α-tocopherol, d-α-tocopherol and l-α-tocopherol.

Also, the term "a 9-cis-retinoic acid-α-tocopherol ester represented by the formula (I)" as used herein refers to all possible optical isomers, racemates and racemic mixtures thereof. These possible, optically active substances may be prepared, for example, according to chiral synthesis using optically active starting materials.

As stated above, the 9-cis-retinoic acid-α-tocopherol ester of this invention itself may exert biological activities to inhibit the proliferation of leukemia cells and induce the differentiation of the said cells. Moreover, a synergistic effect can be achieved by using the present 9-cis-retinoic acid-α-tocopherol ester together with $VD_3$ or 9-cis-RA, while a dose of $VD_3$ or 9-cis-RA can be reduced to prevent $VD_3$ or 9-cis-RA from developing inherent side effects thereto.

The leukemia to which the present therapeutic agent is to be clinically applied includes hematological tumors, that is, leukemia, especially acute promyelocytic leukemia, and lymphoma.

For the treatment of leukemia, therapeutically effective serum concentration of the 9-cis-retinoic acid-α-tocopherol ester in an adult patient weighing 60 kg usually ranges from $1\times10^{-9}$M to $5\times10^{-5}$M in order that the present ester may sufficiently exert its effect. Thus, a specific daily dose for adults to meet the requirement for the serum concentration as stated above may be preferably in the range of from 10 mg to 1200 mg, more preferably from 60 mg to 600 mg, in terms of the 9-cis-retinoic acid-α-tocopherol ester.

The present therapeutic agent which comprises as an active ingredient a combination of the present 9-cis-retinoic acid-α-tocopherol ester with $VD_3$ should be administered at such a dose that can sufficiently exert a synergistic effect of both the ingredients, while the $VD_3$ should be administered at a sufficiently low dose not to produce its side effects, that is to say, at such a dose that its serum concentration in a patient should be $10^{-9}$M or less. A serum concentration of the 9-cis-retinoic acid-α-tocopherol ester in an adult patient weighing 60 kg usually ranges from $1\times10^{-9}$M to $5\times10^{-5}$M in order that the synergistic effect may sufficiently be exerted. Thus, a specific daily dose for adults to meet the requirements for both the serum concentrations as stated above may be preferably in the range of from 10 mg to 1200 mg, more preferably from 60 mg to 600 mg in terms of the 9-cis-retinoic acid-α-tocopherol ester and in the range of from 0.005 μg to 5 μg, more preferably from 0.01 μg to 0.50 μg in terms of $VD_3$. It is essential to administer both the ingredients concomitantly.

The present therapeutic agent which comprises as an active ingredient a combination of the present 9-cis-retinoic acid-α-tocopherol ester with 9-cis-RA should be administered at such a dose that can sufficiently exert a synergistic effect of both the ingredients, while the 9-cis-RA should be administered at a sufficiently low dose not to produce its side effects, that is to say, at such a dose that its serum concentration in a patient should be $10^{-7}$M or less. A serum concentration of the 9-cis-retinoic acid-α-tocopherol ester in an adult patient weighing 60 kg usually ranges from $1\times10^{-9}$M to $5\times10^{-5}$M in order that the synergistic effect may sufficiently be exerted. Then, a specific daily dose for adults to meet the requirements for both the serum concentrations as stated above may be preferably in the range of from 10 mg to 1200 mg, more preferably from 60 mg to 600 mg, in terms of the 9-cis-retinoic acid-α-tocopherol ester and in the range of from 1.0 mg to 80 mg, more preferably from 5.0 mg to 20 mg in terms of 9-cis-RA. It is essential to administer both the ingredients concomitantly.

The therapeutic agent for leukemia according to the present invention may typically be administered via oral, intravenous, subcutaneous, intramuscular or rectal route, and intravenous or oral administration is preferable.

A pharmaceutical composition for treating leukemia according to this invention may be prepared according to any conventional preparation methods. A pharmaceutical preparation for oral administration may include various dosage forms, for example, tablets, granules, powders, hard capsules, soft capsules, liquid preparations for oral administration, etc. A pharmaceutical preparation for parenteral administration may include various dosage forms, for example, injections, suppositories, etc.

These dosage forms can be prepared by any conventional methods using additives commonly used for pharmaceutical preparations, if desired, such as excipients, stabilizers, antiseptics, solubilizers, wetting agents, emulsifying agents, lubricants, sweetening agents, coloring agents, flavors, anti-oxidants and the like. Specific examples of these additives may include starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropylmethylcellulose and the like.

For injections or liquid preparations, the active ingredient may be used in the form of a solution or suspension thereof in a conventional diluent. Typical examples of the diluent may include physiological saline solution, Ringer solution, aqueous glucose solution, alcohols, fatty acid esters, glycols, glycerol, fatty acid glycerides, fats derived from animal and plant sources, paraffins and the like.

Injections may be prepared according to any conventional methods using additives, if required, such as pH adjusters, buffers, stabilizers, preservatives, solubilizing agents and the like.

This invention will be more fully illustrated by way of the following Preparation Example, Examples and Formulation Examples. However, these examples are not to be considered as limiting the present invention.

The medicines and reagents used in the following examples were available as stated below:

Dimethyl sulfoxide (hereinafter referred to as "DMSO") and $VD_3$ were available from Wako Pure Chemical Industries, Ltd. ATRA was available from Sigma Chemical Co. 9-Cis-RA was available from Biomol Research Laboratories or BASF (via Nisshin Badische). Nitro blue tetrazolium (hereinafter referred to as "NBR") and phorbol-12-myristate-13-acetate (hereinafter referred to as "TPA") were available from Sigma Chemical Co.

PREPARATION EXAMPLE 9-cis-retinoic acid-α-tocopherol ester

To a solution of 50 mg (0.1664 mmol) of 9-cis-retinoic acid (9-cis-RA) in diisopropyl ether (5 ml) was added 26 μl (0.1831 mmol) of trifluoroacetic acid anhydride and the mixture was stirred at room temperature for 15 minutes. Then, a solution of 79 mg (0.1831 mmol) of dl-α-tocopherol in diisopropyl ether (5 ml) was added dropwise and the mixture was stirred at room temperature for one hour. To the reaction mixture was added 28% (w/v) aqueous ammonia (10 ml) and the resulting mixture was extracted with diisopropyl ether (20 ml×3). The combined organic layers were washed successively with water and saturated aqueous sodium chloride. The diisopropyl ether layer was dried over anhydrous sodium sulfate and the solvent was then distilled off under reduced pressure. The residue was purified by a silica gel chromatography and the fractions from hexane containing 2% (v/v) diisopropyl ether gave 36 mg (30%) of the title compound as a yellow oily substance.

$^1$H NMR (CDCl$_3$, 400 MHz) d 0.82–0.90(m, 12H), 1.00–2.20(m, 29H), 1.05(s, 3H), 1.55(s, 6H), 1.66(s, 3H), 1.98(s, 3H), 2.03(s, 6H), 2.09(s, 3H), 2.40(s, 3H), 2.59(t, J=6.8 Hz, 2H), 6.08(s, 1H), 6.09(d, J=10.7 Hz, 1H), 6.29(d, J=13.2 Hz, 1H), 6.33(d, J=14.2 Hz, 1H), 6.67(d, J=15.6 Hz, 1H), 7.15(dd, J=11.7 Hz, 15.0 Hz, 1H)

General Notes:

Cultured cells and culture conditions:

The cultured cell used for the following determination and examples was the NB4 cell, i.e., the cultured cell of human myelomonocytic leukemia, which was given from Professor H. Phillip Koeffler of Cedars-Sinai Medical Center/UCLA School of Medicine, Los Angels, U.S.A. (Blood, Vol. 77, 1080, 1991) and used here after suspending and incubating in RPMI 1640 medium (manufactured by Gibco BRL) containing 10% fetal bovine serum (hereinafter referred to as "FBS") and 80 μg/ml gentamicin at 37° C. in a moist air containing 5% $CO_2$.

Proliferation of cultured cells and determination for differentiation of cultured cells:

The above cultured cells were incubated in a culture plate under the same conditions as described above with the addition of 9-cis-retinoic acid-α-tocopherol ester alone or in combination with $VD_3$, ATRA or 9-cis-RA.

The number of cultured cells was measured by means of Coulter Counter type ZM (manufactured by Coulter Electronics Co., Ltd., U.K.).

NBT reducing activity values were measured as a standard for the differentiation induction of the cultured cells of myelomonocytic leukemia according to the following method:
1) Preparation of NBT test solution: To 100 ml of RPMI 1640 medium containing 10% FBS was added a solution of 100 mg of NBT in 1 ml of DMSO and then 100 μl of a DMSO solution of TPA at 100 μg/ml, and the resulting mixture was stirred well to prepare a NBT test solution.
2) The cultured cells were placed into a 10 ml-test tube and the number of the cultured cells was measured. Thereafter, the test tube was centrifuged, a supernatant was discarded and then 1 ml aliquot of the said NBT test solution was added to each test tube. The resulting mixture was shaken at 37° C. for 30 minutes. The reaction was discontinued by adding 0.3 ml of 5N hydrochloric acid and then the mixture was allowed to stand at room temperature for 1–2 hours. The cultured cell suspension thus obtained was centrifuged to remove a supernatant, 0.7 ml of DMSO was added and then absorbance was measured at 560 nm by means of a spectrophotometer (type U-2000, manufactured by Hitachi, Ltd.). The measured data was converted to the absorbance per 1 cultured cells, which was designated as a NBT reducing activity value.

An increased NBT reducing activity value means a promoted differentiation induction of leukemia cells.

EXAMPLE 1

Combined effect of 9-cis-retinoic acid-α-tocopherol ester and $VD_3$ on the differentiation induction of NB4 cells To NB4 cells ($2\times10^5$ cells/ml) used as the cultured cell was added $VD_3$ so as to provide concentrations of $3\times10^{-9}M$, $3\times10^{-8}M$ and $3\times10^{-7}M$, respectively, and then 9-cis-retinoic acid-α-tocopherol ester was further added so as to provide a concentration of $3\times10^{-6}M$. Incubation was carried out for 4 days to investigate the combined effect on the differentiation induction of the cells. For comparison, the cultured cells not containing any 9-cis-retinoic acid-α-tocopherol ester and those containing tretinoin tocoferil ($3\times10^{-6}M$) instead of the 9-cis-retinoic acid-α-tocopherol ester were similarly incubated. The effect on the differentiation induction of the cells was investigated by measuring NBT reducing activity values. The results are shown in FIG. 1.

Figure 1:
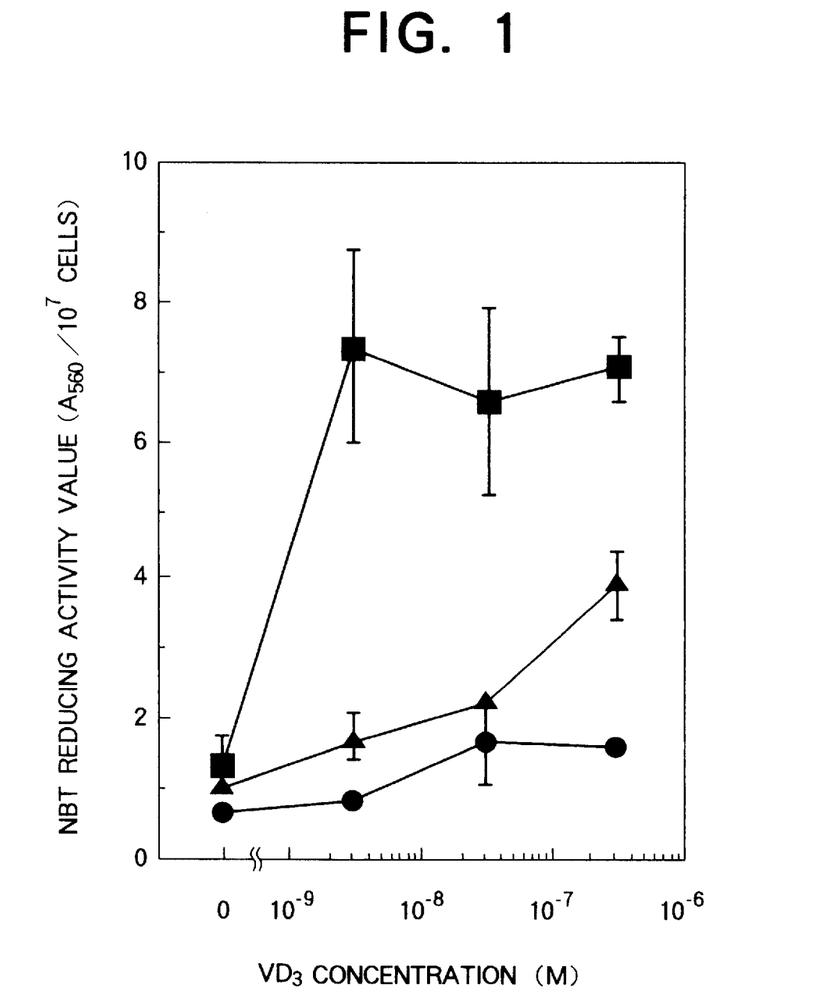
FIG. 1 is a graph showing a relationship between $VD_3$ concentrations and NBT reducing activity values obtained in the cases where $VD_3$ was used alone (-●-), where 9-cis-retinoic acid-α-tocopherol ester was used together with $VD_3$ (-■-) and where tretinoin tocoferil was used together with $VD_3$ (-▲-), all being applied to NB4 cells.

In FIG. 1, the abscissa and ordinate indicate concentrations of $VD_3$ and absorbances (i.e., NBT reducing activity values) per $10^7$ cultured cells, respectively. The line represented by (-●-) shows a relationship between concentrations of $VD_3$ and NBT reducing activity values when $VD_3$ was used alone, the line represented by (-■-) shows a relationship between concentrations of $VD_3$ and NBT reducing activity values when 9-cis-retinoic acid-α-tocopherol ester ($3\times10^{-6}M$) was used together with $VD_3$, and the line represented by (-▲-) shows a relationship between concentrations of $VD_3$ and NBT reducing activity values when tretinoin tocoferil ($3\times10^{-6}M$) was used together with $VD_3$.

FIG. 1 shows that a NBT reducing ability was not increased in a concentration range of up to $3.0\times10^{-6}M$ when $VD_3$ was used alone, while tretinoin tocoferil ($3\times10^{-6}M$), when used together, potentiated a NBT reducing ability by $VD_3$, but its potentiating ability was limited to approximately three-fold level at $3\times10^{-9}M$ of $VD_3$. On the other hand, 9-cis-retinoic acid-α-tocopherol ester ($3\times10^{-6}M$), when used together, potentiated a NBT reducing ability by $VD_3$ and its potentiating ability was raised to approximately 7.5-fold level at $3\times10^{-9}M$ of $VD_3$. Accordingly, it is clearly demonstrated that 9-cis-retinoic acid-α-tocopherol ester could noticeably potentiate the differentiation of NB4 cells by $VD_3$ and its potentiating effect was far more strong as compared with tretinoin tocoferil.

EXAMPLE 2

Combined effect of 9-cis-retinoic acid-α-tocopherol ester and 9-cis-RA on the inhibition of NB4 cell proliferation To NB4 cells ($5\times10^5$ cells/ml) used as the cultured cell was added 9-cis-RA ($3\times10^{-9}M$) and then 9-cis-retinoic acid-α-tocopherol ester was further added so as to provide a concentration of $3\times10^{-6}M$. Incubation was carried out for 4 days to investigate the inhibitory effect on the cell proliferation. For comparison, the cultured cells not containing both 9-cis-retinoic acid-α-tocopherol ester and 9-cis-RA (Control), those not containing any 9-cis-retinoic acid-α-tocopherol ester and those containing tretinoin tocoferil ($3\times10^{-6}M$) instead of the 9-cis-retinoic acid-α-tocopherol ester were similarly incubated. After 4 days, the number of the cells was counted and expressed in terms of a relative percent calculated from the cell number of the Control defined as 100. The results are shown in FIG. 2.

Figure 2:
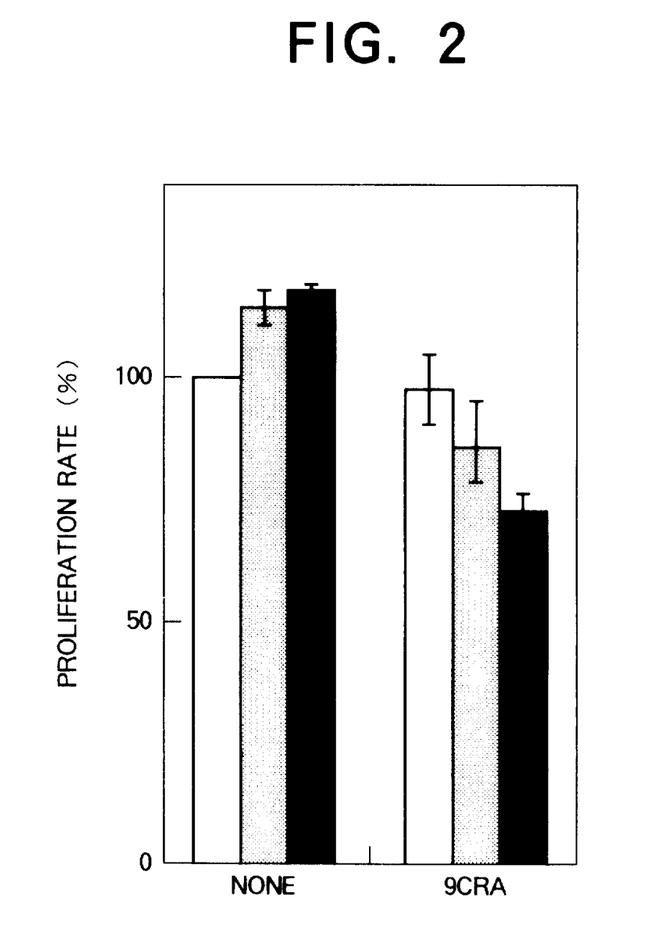
FIG. 2 is a bar graph showing inhibitory effects on the proliferation of NB4 cells in terms of percent (%) proliferation obtained in the cases where 9-cis-RA ($3\times10^{-9}$M), 9-cis-retinoic acid-α-tocopherol ester ($3\times10^{-6}$M) and tretinoin tocoferil ($3\times10^{-6}$M) were used alone, respectively, and where 9-cis-RA ($3\times10^{-9}$M) was used together with 9-cis-retinoic acid-α-tocopherol ester ($3\times10^{-6}$M) or tretinoin tocoferil ($3\times10^{-6}$M), all being applied to NB4 cells.

In FIG. 2, the symbols of None and 9CRA shown beneath the abscissa represent the group not given 9-cis-RA and the group given 9-cis-RA, respectively. The columns from the left to the right in order represent the Control (not given any active agents), the group given tretinoin tocoferil alone ($3\times10^{-6}M$), the group given 9-cis-retinoic acid-α-tocopherol ester alone ($3\times10^{-6}M$), the group given 9-cis-RA alone ($3\times10^{-9}M$), the group given concomitantly 9-cis-RA ($3\times10^{-9}M$) and tretinoin tocoferil ($3\times10^{-6}M$) and the group given concomitantly 9-cis-RA ($3\times10^{-9}M$) and 9-cis-retinoic acid-α-tocopherol ester ($3\times10^{-6}M$), respectively.

FIG. 2 shows that the proliferation of NB4 cells could not be inhibited with 9-cis-RA alone ($3\times10^{-9}M$), while tretinoin tocoferil ($3\times10^{-6}M$) could inhibit the proliferation of NB4 cells when used together with 9-cis-RA ($3\times10^{-9}M$), but its inhibition rate (i.e., a relative percent of the number of survival cells to that of the Control) was approximately 86%. In contrast thereto, when 9-cis-retinoic acid-α-tocopherol ester ($3\times10^{-6}M$) was used together, the proliferation of NB4 cells was inhibited and its inhibition rate was approximately 72%, which means the proliferation of NB4 cells was noticeably inhibited. Accordingly, it is clearly demonstrated that the differentiation of NB4 cells can be effectively inhibited by a combined use of 9-cis-retinoic acid-α-tocopherol ester with 9-cis-RA and the inhibitory effect was far more potent as compared with that of tretinoin tocoferil.

EXAMPLE 3

Combined effect of 9-cis-retinoic acid-α-tocopherol ester and 9-cis-RA on the differentiation induction of NB4 cells To NB4 cells ($5\times10^5$ cells/ml) used as the cultured cell was added 9-cis-RA ($3\times10^{-9}M$) and then 9-cis-retinoic acid-α-tocopherol ester at a concentration of $3\times10^{-6}M$. Incubation was carried out for 4 days. The cells were washed with a phosphate buffer and then reacted with a mouse monoclonal antibody CD11b (obtained from Nichirei Corporation) [diluted with IFA buffer (10 mM Hepes, pH 7.4, 150 mM NaCl, 4% FBS, 0.1% sodium azide] at 4° C. for one hour. The cells were washed twice with IFA buffer and then reacted with a FITC-labeled rabbit anti-mouse antibody (diluted with IFA buffer) at 4° C. for one hour. The cells were washed twice with IFA buffer and fluorescence-positive cells were analyzed by means of a flow cytometry (Epics XL, manufactured by Coulter Electronics Co., Ltd.). For comparison, the cultured cells not containing both 9-cis-retinoic acid-α-tocopherol ester and 9-cis-RA, those containing 9-cis-RA ($3\times10^{-9}M$), those containing 9-cis-retinoic acid alone ($3\times10^{-8}M$) and those containing tretinoin tocoferil ($3\times10^{-6}M$) instead of the 9-cis-retinoic acid-α-tocopherol ester were similarly incubated and reacted with the antibodies. Appearance of a differentiation marker for CD11b indicates the differentiation of the cells into a granulocyte system. The results are shown in FIG. 3.

Figure 3:
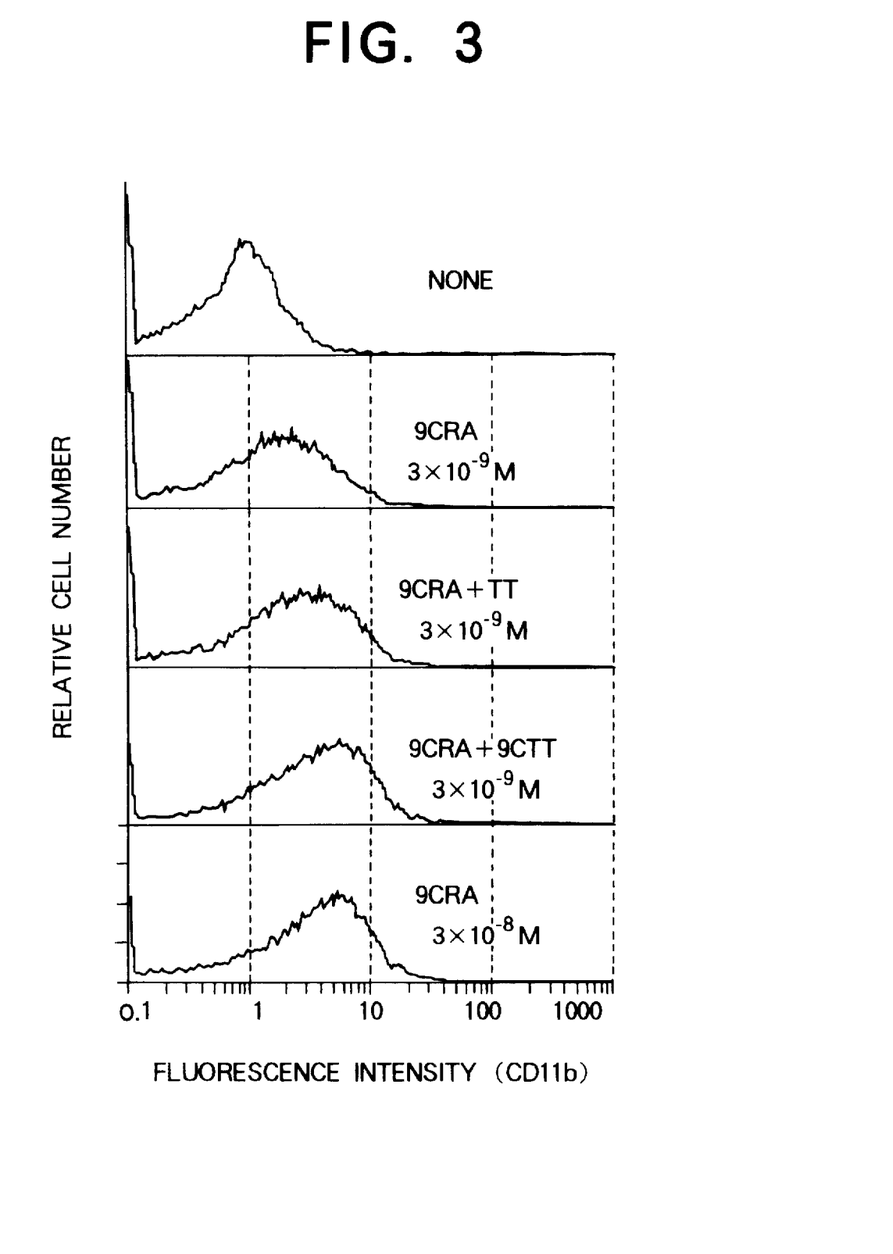
FIG. 3 is a graph showing a relationship between fluorescence intensities of a differentiation marker (CD11b) and the number of cells obtained in the cases where 9-cis-RA was used alone ($3\times10^{-9}$M or $3\times10^{-8}$M) and where 9-cis-RA ($3\times10^{-9}$M) was used together with 9-cis-retinoic acid-α-tocopherol ester ($3\times10^{-6}$M) or tretinoin tocoferil ($3\times10^{-6}$M), all being applied to NB4 cells.

In FIG. 3, the symbols of None and 9CRA represent the group not given 9-cis-RA and the group given 9-cis-RA, respectively, while the symbols of 9CRA+TT and 9CRA+9CTT represent the group given 9-cis-RA ($3\times10^{-9}$M) and tretinoin tocoferil ($3\times10^{-6}$M) and the group given 9-cis-RA ($3\times10^{-9}$M) and 9-cis-retinoic acid-α-tocopherol ester ($3\times10^{-6}$M) respectively.

FIG. 3 shows that differentiation could be far more induced when tretinoin tocoferil ($3\times10^{-6}$M) was further added as compared when 9-cis-RA ($3\times10^{-9}$M) was used alone. Further, differentiation could be much more noticeably induced when 9-cis-retinoic acid-α-tocopherol ester ($3\times10^{-6}$M) was further added as compared when tretinoin tocoferil ($3\times10^{-6}$M) was further added and the differentiation inducing ability was equivalent to that when 9-cis-retinoic acid ($3\times10^{-8}$M) was used alone. Accordingly, it is clearly demonstrated that an equivalent effect can be achieved by a combination of 9-cis-retinoic acid with 9-cis-retinoic acid-α-tocopherol ester even if an amount of the 9-cis-retinoic acid to be used may be reduced to 1/10.

EXAMPLE 4

Inhibitory effects on proliferation of NB4 cells by 9-cis-retinoic acid-α-tocopherol ester alone and by combined use of the ester with $VD_3$ To NB4 cells ($5\times10^5$ cells/ml) used as the cultured cell was added 9-cis-retinoic acid-α-tocopherol ester was added ($1.5\times10^{-5}$M). Incubation was carried out for 4 days. For comparison, the cultured cells not containing any active compounds and those containing tretinoin tocoferil ($1.5\times10^{-5}$M) instead of the 9-cis-retinoic acid-α-tocopherol ester were similarly incubated. In order to investigate the effect obtained by a combined use with $VD_3$, the cultured cells containing 9-cis-retinoic acid-α-tocopherol ester ($1.5\times10^{-5}$M) and $VD_3$ ($3\times10^{-9}$M) and for comparison those containing tretinoin tocoferil ($1.5\times10^{-5}$M) and $VD_3$ ($3\times10^{-9}$M) were similarly incubated. The results are shown in FIG. 4.

Figure 4:
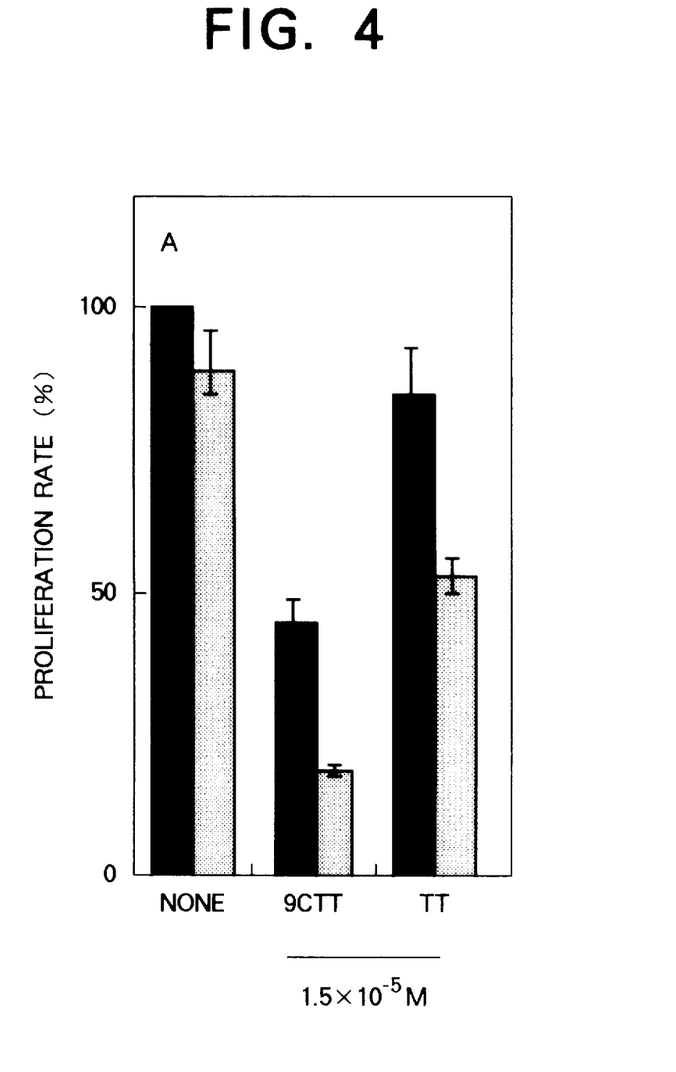
FIG. 4 is a bar graph showing an inhibitory effect on the proliferation of NB4 cells in terms of percent (%) proliferation obtained in the cases where $VD_3$ ($3\times10^{-9}$M), 9-cis-retinoic acid-α-tocopherol ester ($1.5\times10^{-5}$M) and tretinoin tocoferil ($1.5\times10^{-5}$M) were used alone, respectively, and where $VD_3$ ($3\times10^{-9}$M) was used together with 9-cis-retinoic acid-α-tocopherol ester ($1.5\times10^{-5}$M) or tretinoin tocoferil ($1.5\times10^{-5}$M), all being applied to NB4 cells.

In FIG. 4, the symbols of None, 9CTT and TT shown beneath the abscissa represent the group not given 9-cis-retinoic acid-α-tocopherol ester or tretinoin tocoferil, the group given 9-cis-retinoic acid-α-tocopherol ester ($1.5\times10^{-5}$M) and the group given tretinoin tocoferil ($1.5\times10^{-5}$M), respectively. The columns from the left to the right in order represent the Control (not given any active agents), the group given $VD_3$ alone ($3\times10^{-9}$M), the group given 9-cis-retinoic acid-α-tocopherol ester alone ($1.5\times10^{-5}$M), the group given $VD_3$ ($3\times10^{-9}$M) together with 9-cis-retinoic acid-α-tocopherol ester ($1.5\times10^{-5}$M), the group given tretinoin tocoferil alone ($1.5\times10^{-5}$M) and the group given $VD_3$ ($3\times10^{-9}$M) together with tretinoin tocoferil ($1.5\times10^{-5}$M), respectively.

FIG. 4 shows that 9-cis-retinoic acid-α-tocopherol ester even when used alone could highly inhibit the proliferation of NB4 cells and its inhibitory effect was far more potent than that of tretinoin tocoferil when used alone. FIG. 4 further shows that 9-cis-retinoic acid-α-tocopherol ester ($1.5\times10^{-5}$M) could noticeably potentiate an inhibitory effect on the proliferation by $VD_3$ and this inhibitory effect was much more effective than that when tretinoin tocoferil ($1.5\times10^{-5}$M) and $VD_3$ ($3\times10^{-9}$M) were used together.

EXAMPLE 5

Cell differentiation inducing effect by 9-cis-retinoic acid-α-tocopherol ester

To NB4 cells ($5\times10^5$ cells/ml) used as the cultured cell was added 9-cis-retinoic acid-α-tocopherol ester ($1.5\times10^{-5}$M) and incubation was carried out for 4 days to investigate the effect on the differentiation induction of the cells. For comparison, the cultured cells not containing 9-cis-retinoic acid-α-tocopherol ester and those containing tretinoin tocoferil ($1.5\times10^{-5}$M) were similarly incubated. On the other hand, for investigating the effect by a combined use with $VD_3$, the cultured cells containing 9-cis-retinoic acid-α-tocopherol ester ($1.5\times10^{-5}$M) and $VD_3$ ($3\times10^{-9}$M) and for comparison those containing tretinoin tocoferil ($1.5\times10^{-5}$M) instead of the 9-cis-retinoic acid-α-tocopherol ester and $VD_3$ ($3\times10^{-9}$M) were also similarly incubated. The effect on the differentiation induction of the cells was investigated by measuring NBT reducing activity values. The results are shown in FIG. 5.

Figure 5:
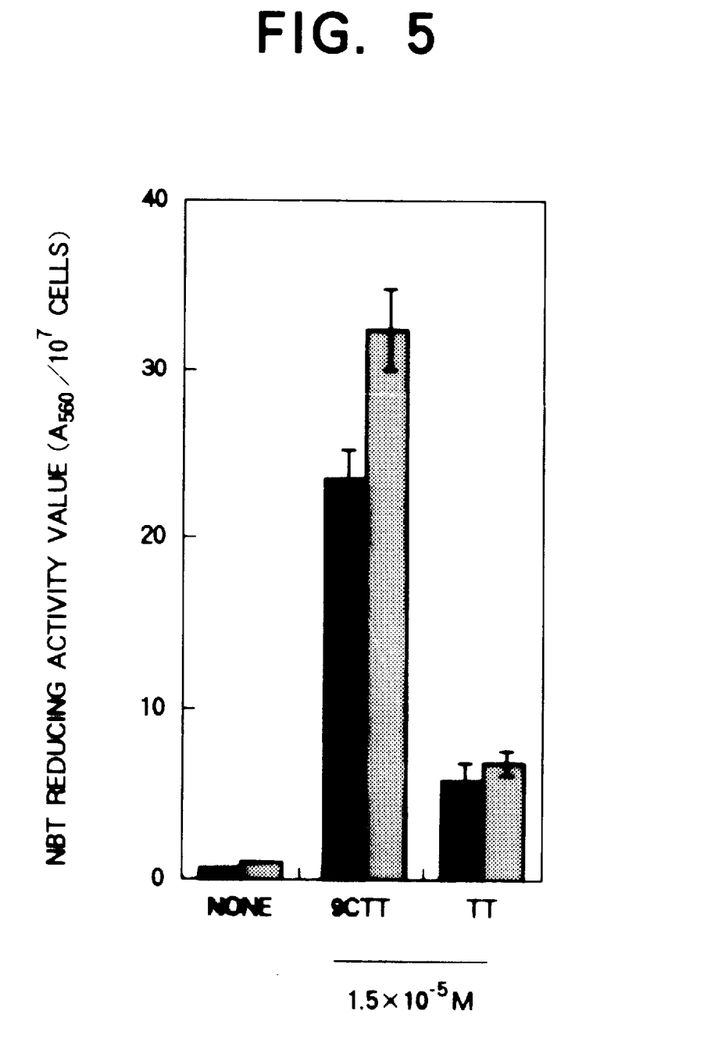
FIG. 5 is a bar graph showing NBT reducing activity values obtained in the cases where $VD_3$ ($3\times10^{-9}$M), 9-cis-retinoic acid-α-tocopherol ester ($1.5\times10^{-5}$M) and tretinoin tocoferil ($1.5\times10^{-5}$M) were used alone, respectively, and where $VD_3$ ($3\times10^{-9}$M) was used together with 9-cis-retinoic acid-α-tocopherol ester ($1.5\times10^{-5}$M) or tretinoin tocoferil ($1.5\times10^{-5}$M), all being applied to NB4 cells.

In FIG. 5, the ordinate indicates absorbances (NBT reducing activity values) per $10^7$ cultured cells, while the symbols of None, 9CTT and TT shown beneath the abscissa represent the group not given 9-cis-retinoic acid-α-tocopherol ester or tretinoin tocoferil, the group given 9-cis-retinoic acid-α-tocopherol ester ($1.5\times10^{-5}$M) and the group given tretinoin tocoferil ($1.5\times10^{-5}$M), respectively. The columns from the left to the right in order represent the Control (not given any active agents), the group given $VD_3$ alone ($3\times10^{-9}$M), the group given 9-cis-retinoic acid-α-tocopherol ester alone ($1.5\times10^{-5}$M), the group given 9-cis-retinoic acid-α-tocopherol ester ($1.5\times10^{-5}$M) together with $VD_3$ ($3\times10^{-9}$M), the group given tretinoin tocoferil alone ($1.5\times10^{-5}$M), and the group given tretinoin tocoferil ($1.5\times10^{-5}$M) together with $VD_3$ ($3\times10^{-9}$M), respectively.

FIG. 5 shows that 9-cis-retinoic acid-α-tocopherol ester ($1.5\times10^{-6}$M) even when used alone could noticeably raise a NBT reducing ability and this effect was far more potent than that of tretinoin tocoferil when used alone ($1.5\times10^{-5}$M). FIG. 5 further shows that 9-cis-retinoic acid-α-tocopherol ester ($1.5\times10^{-5}$M) could noticeably potentiate an inhibitory effect on the proliferation by $VD_3$ and this inhibitory effect was much more effective than that when tretinoin tocoferil ($1.5\times10^{-5}$M) and $VD_3$ ($3\times10^{-9}$M) were used together. Accordingly, it is clearly demonstrated that 9-cis-retinoic acid-α-tocopherol ester can highly induce the differentiation of NB4 cells and potentiate the differentiation of NB4 cells by $VD_3$.

In summary, the three types of the present pharmaceutical preparations for treating leukemia may far more effectively inhibit the proliferation of leukemia cells and noticeably promote the differentiation induction of the cells. Moreover, they are still effective for the treatment of leukemia even at a serum $VD_3$ concentration of $10^{-9}$M or less which dose not cause any side effects. In addition to this, a dose of 9-cis-RA may be reduced to such a level not developing any side effects, which is highly useful in the treatment of leukemia.

FORMULATION EXAMPLE 1

Soft capsules for oral administration 50 g of 9-cis-retinoic acid-α-tocopherol ester was mixed with 130 g of coconut oil to form a homogeneous solution. Separately, a gelatin solution for capsule coating was prepared from 93 g of gelatin, 19 g of glycerol, 10 g of D-sorbitol (70 w/v %), 0.4 g of ethyl p-hydroxybenzoate, 0.2 g of propyl p-hydroxybenzoate and 0.4 g of titanium oxide. Soft capsules were prepared from the two solutions prepared as above according to a manual plate stamping method, each capsule containing 180 mg of 9-cis-retinoic acid-α-tocopherol ester.

FORMULATION EXAMPLE 2

Injections 5 g of 9-cis-retinoic acid-α-tocopherol ester, a proper volume of soybean oil and 1 g of benzyl alcohol were mixed and then made up to a total volume of 100 cc with soybean oil. The resulting solution was aseptically injected portionwise into ampoules in each portion of 2 cc and then the ampoules were sealed.

FORMULATION EXAMPLE 3

Soft capsules for oral administration 50 g of 9-cis-retinoic acid-α-tocopherol ester and 5 μg of $VD_3$ were mixed with 130 g of coconut oil to form a homogeneous solution. Separately, a gelatin solution for capsule coating was prepared from 93 g of gelatin, 19 g of glycerol, 10 g of D-sorbitol (70 w/v %), 0.4 g of ethyl p-hydroxybenzoate, 0.2 g of propyl p-hydroxybenzoate and 0.4 g of titanium oxide. Soft capsules were prepared from the two solutions prepared as above according to a manual plate stamping method, each capsule containing 180 mg of 9-cis-retinoic acid-α-tocopherol ester and 0.018 μg of $VD_3$.

FORMULATION EXAMPLE 4

Injections 5 g of 9-cis-retinoic acid-α-tocopherol ester, 0.5 μg of $VD_3$, a proper volume of soybean oil and 1 g of benzyl alcohol were mixed and then made up to a total volume of 100 cc with soybean oil. The resulting solution was aseptically injected portionwise into ampoules in each portion of 2 cc and then the ampoules were sealed.

FORMULATION EXAMPLE 5

Soft capsules for oral administration 50 g of 9-cis-retinoic acid-α-tocopherol ester and 2.8 g of 9-cis-RA were mixed with 130 g of coconut oil to form a homogeneous solution. Separately, a gelatin solution for capsule coating was prepared from 93 g of gelatin, 19 g of glycerol, 10 g of D-sorbitol (70 w/v %), 0.4 g of ethyl p-hydroxybenzoate, 0.2 g of propyl p-hydroxybenzoate and 0.4 g of titanium oxide. Soft capsules were prepared from the two solutions prepared as above according to a manual plate stamping method, each capsule containing 180 mg of 9-cis-retinoic acid-α-tocopherol ester and 10 mg of 9-cis-RA.

FORMULATION EXAMPLE 6

Injections 5 g of 9-cis-retinoic acid-α-tocopherol ester, 280 mg of 9-cis-RA, a proper volume of soybean oil and 1 g of benzyl alcohol were mixed and then made up to a total volume of 100 cc with soybean oil. The resulting solution was aseptically injected portionwise into ampoules in each portion of 2 cc and then the ampoules were sealed.

What is claimed is:

1. A method of inducing the differentiation of leukemia cells in a patient in need thereof comprising treating said patient with an effective amount of the 9-cis-retinoic acid-α-tocopherol ester represented by formula (I):

thereby inducing differentiation of said cells.

2. The method of claim 1, wherein said effective amount is a daily dose of 10 to 1200 mg for an adult patient.

3. The method of claim 1, wherein said effective amount is a daily dose of 60 to 600 mg for an adult patient.

* * * * *